(12) United States Patent
Pavlin

(10) Patent No.: US 8,636,506 B2
(45) Date of Patent: Jan. 28, 2014

(54) DIFFERENTIAL VIBRATION OF DENTAL PLATE

(75) Inventor: Dubravko Pavlin, Houston, TX (US)

(73) Assignee: OrthAccel Technologies, Inc., Bellaire, TX (US)

( * ) Notice: Subject to any disclaimer, the term of this patent is extended or adjusted under 35 U.S.C. 154(b) by 0 days.

(21) Appl. No.: 13/000,557

(22) PCT Filed: Jun. 22, 2009

(86) PCT No.: PCT/US2009/048086
§ 371 (c)(1),
(2), (4) Date: Dec. 14, 2011

(87) PCT Pub. No.: WO2009/158297
PCT Pub. Date: Dec. 30, 2009

(65) Prior Publication Data
US 2012/0094246 A1    Apr. 19, 2012

Related U.S. Application Data

(60) Provisional application No. 61/074,884, filed on Jun. 23, 2008.

(51) Int. Cl.
    *A61C 3/00*  (2006.01)
(52) U.S. Cl.
    USPC .................................. 433/6; 433/24
(58) Field of Classification Search
    USPC .......................... 433/6, 18–21, 24
    See application file for complete search history.

(56) References Cited

U.S. PATENT DOCUMENTS

| 3,482,312 | A |   | 12/1969 | Smith |
| 3,802,302 | A |   | 4/1974 | Bengtson |
| 4,244,688 | A |   | 1/1981 | Kurz |
| 4,348,177 | A |   | 9/1982 | Kurz |
| 4,382,780 | A |   | 5/1983 | Kurz |
| 4,531,916 | A |   | 7/1985 | Scantlebury et al. |
| 4,629,424 | A | * | 12/1986 | Lauks et al. ............ 433/6 |
| 4,763,791 | A |   | 8/1988 | Halverson et al. |
| 4,883,046 | A |   | 11/1989 | Fontenot |
| 4,955,393 | A |   | 9/1990 | Adell |
| 5,030,098 | A |   | 7/1991 | Branford |
| 5,336,092 | A |   | 8/1994 | Chalifoux |
| 5,645,878 | A |   | 7/1997 | Breslin et al. |
| 5,967,784 | A | * | 10/1999 | Powers ............ 433/229 |
| 6,089,864 | A | * | 7/2000 | Buckner et al. .......... 433/71 |
| 6,632,088 | B2 |  | 10/2003 | Voudouris |
| 6,633,747 | B1 | * | 10/2003 | Reiss .............. 455/41.2 |
| 6,648,639 | B2 |  | 11/2003 | Mao |
| 6,832,912 | B2 |  | 12/2004 | Mao |

(Continued)

FOREIGN PATENT DOCUMENTS

| JP | 2007260158 A | 10/2007 |
| WO | WO2007/146703 | 12/2007 |
| WO | 2009158297 | 12/2009 |
| WO | WO2010/093632 | 8/2010 |

OTHER PUBLICATIONS

U.S. Appl. No. 61/040,777, "Vibrating Compressible Dental Plate for Correcting Malocclusion".

*Primary Examiner* — Ralph Lewis
(74) *Attorney, Agent, or Firm* — Boulware & Valoir

(57) ABSTRACT

An improved vibrating dental plate that allows differential vibration of one or more teeth to assist in orthodontic remodeling is provided.

13 Claims, 3 Drawing Sheets

(56) References Cited

U.S. PATENT DOCUMENTS

| | | |
|---|---|---|
| 6,852,774 B1 | 2/2005 | Engelbrecht |
| 7,029,276 B2 | 4/2006 | Mao |
| 7,163,399 B2 | 1/2007 | Kajimoto et al. |
| 7,192,281 B2 | 3/2007 | Mailyan |
| 8,079,966 B2 * | 12/2011 | El-Bialy et al. ............... 601/2 |
| 8,123,520 B2 * | 2/2012 | Yamamoto et al. ............ 433/18 |
| 2006/0287620 A1 | 12/2006 | Tseng |
| 2007/0161461 A1 | 7/2007 | Nguyen |
| 2007/0161931 A1 | 7/2007 | Kunita et al. |
| 2007/0179414 A1 | 8/2007 | Imboden et al. |
| 2007/0208284 A1 | 9/2007 | Huang |
| 2007/0255188 A1 | 11/2007 | Tseng |
| 2007/0299372 A1 | 12/2007 | Chang |
| 2008/0227046 A1 | 9/2008 | Lowe et al. |
| 2008/0227047 A1 | 9/2008 | Lowe et al. |
| 2011/0136070 A1 * | 6/2011 | Rubin et al. ............... 433/2 |

* cited by examiner

DIFFERENTIAL VIBRATION OF DENTAL PLATE

CROSS REFERENCE TO RELATED APPLICATIONS

This application claims priority to U.S. Provisional Application 61/074,884, filed Jun. 23, 2008, incorporated by reference.

FEDERALLY SPONSORED RESEARCH STATEMENT

Not applicable.

REFERENCE TO MICROFICHE APPENDIX

Not applicable.

FIELD OF THE INVENTION

The invention relates to systems and methods for correcting malocclusion, and in particular to a device that corrects occlusion via the differential vibration of one or more teeth.

BACKGROUND OF THE INVENTION

Orthodontics is a dental specialty that treats malocclusion through the movement of teeth as well as control and modification of facial growth. This process is usually accomplished by using a continuous mechanical force to induce bone remodeling, thereby enabling the teeth to move to a better position. In this approach, orthodontic appliances provide a continuous static force to the teeth via an archwire connected to brackets affixed to each tooth. As the teeth slowly move due to the force, the arch wires are adjusted to increase the force. Although effective, this widely accepted approach takes about twenty four months on average to achieve success.

Dental researchers have long postulated that a pulsating force might also be used to move teeth efficiently or to ease the pain of traditional orthodontics.

For example, U.S. Pat. Nos. 4,244,688, 4,348,177 and 4,382,780 describe devices used to vibrate the teeth during orthodontic treatment, although each uses a different means of applying a vibration. The U.S. Pat. No. 4,244,688 employs a cumbersome external power source to power one to four small motors, whereas U.S. Pat. No. 4,348,177 uses pulsating fluids moved with the chewing motion of the jaw, and U.S. Pat. No. 4,382,780 uses a radio and speaker to set up a vibration. These devices are mounted on a bulky headgear that surrounds the head and are connected directly to the teeth by its intraoral portions. The devices are cumbersome, difficult to construct, expensive and are very difficult to use, thus reducing patient compliance.

U.S. Pat. No. 5,030,098 by Branford describes a hand-held device that simulates chewing in order to treat periodontal disease by increasing blood flow to the gums. The mouthpiece has a perforated malleable plate such that biting of the mouthpiece results in the plate adapting to the user's bite which, of course, varies with each user. The external vibrator imparts motion to the mouthpiece and thus the user's teeth. The device, however, uses an external power source. Further, the dental plate is brass, and is very unpleasant to bite on.

U.S. Pat. No. 5,967,784 by Powers describes a similar device to that described by Brandford. It too is a hand-held tooth vibrator that is simple and has an exterior motor housing connected to a vibrating interdental mouthpiece portion for gripping between the teeth of the patient. The exterior housing contains a battery and a switch for selectively operating a motor with an off-center weight attached to the motor rotating shaft for creating a high frequency vibration that vibrates the entire device. The mouthpiece is disposable, making the system affordable and more convenient to use. The patent teaches using the device to alleviate pain by inserting the interdental mouthpiece between the teeth and clenching and releasing the teeth over the mouthpiece, in an attempt to engage as many teeth as possible in the transmitted vibrations. The vibration is believed to alleviate pain by increasing blood flow.

The devices of Branford and Powers are superficially similar to those of the invention herein, but there are significant differences. Most importantly, there is no recognition in either patent that the vibratory device can be used for tooth remodeling or movement. Thus, the shape of the dental plate in each case is a very flat U- or Y-shaped member that is largely ineffective for remodeling. Additionally, the vibration is not optimized in frequency and amplitude for remodeling. Finally, neither device is programmable, nor can teeth be differentially vibrated, thus the dentist cannot optimize its usage for each patient, nor monitor patient compliance. All of these shortcomings reduce the effectiveness of these devices for remodeling uses.

U.S. Pat. No. 6,632,088 describes a bracket with powered actuator mounted thereto to provide vibration, but this device appears to also be held completely internally to the patients mouth, thus again being cumbersome, and thus may affect patient comfort and ultimately patient acceptance of the device.

Mao was probably the first to show that the use of cyclic forces could improve dental straightening in rabbits (see U.S. Pat. Nos. 6,684,639, 6,832,912, 7,029,276). Certain dynamic loading patterns (cycling force with rest periods) were shown to greatly increase bone formation compared to basic dynamic loading. Inserting rest periods is now known to be especially efficacious as it allows mechanosensitivity to be restored to the bone tissue. A point of diminishing returns is reached within each loading session. Therefore, intermittently loading cyclic force can increase the rate of bone formation significantly.

However, the device provided by Mao uses arch wires and brackets with a centrally mounted motor that is held inside the mouth. Therefore, the device is uncomfortable for the patent to use, and there is always some risk of electric shock.

Kajimoto, U.S. Pat. No. 7,163,399, describes a device capable of differential vibration. It is an ultrasonic therapy device with an oscillator embedded in the body and holding members which hold the body next to the affected area. The bodies are fixed in the oral cavity next to an implant to accelerate osteogenesis around implant fixtures by supplying an ultrasonic signal from an external driver to the oscillator. This device is only used with an implant, and does not appear suitable for general orthodontic use.

Mailyan, U.S. Pat. No. 7,192,281, also describes a vibrational system for encouraging osteogenesis. Mailyan inserts plates at growth zones for palatal and jaw defect repair. The plates are vibrated to stimulate neogenesis of bone tissue, and then resized to allow further growth. The process uses the mechanical forces of the jaw to apply pressure to missing palate or jaw defect.

JP2007260158 describes a device capable of differential vibration by virtue of holes in the bite plate. Thus, no vibration is transmitted to those teeth in the holes. Each device however, must be custom made for the patient in order to have the correct fit and hole placement.

What is required is a simple, affordable device that is optimized to stimulate osteogenesis and accelerate tooth movement for patients who only need remodeling of one tooth or the teeth in one or more quadrants. Preferably the device can be used with all existing orthodontic devices or can be used alone to remodel tooth alignment.

SUMMARY OF THE INVENTION

This invention continues the work described in U.S. application Ser. Nos. 11/773,849, 11/773,858, and 61/040,777 incorporated herein by reference, but presents an improvement thereon that allows the treatment of an individual tooth or groups of teeth. The prior inventions were generally based on vibrating the entire dentition, which allows for the motor (and battery) to be placed externally, thus simplifying the design and manufacture and reducing cost. However, there are instances where it would be desirable to target a single tooth or a group of teeth for treatment, without vibrating the entire dental plate.

Therefore, this invention modifies the prior inventions to allow only a specific area of the bite-plate to vibrate (differential vibration), as determined by the orthodontist. For example, in FIG. 1 the differential dental vibrator would allow the orthodontist to only vibrate area A. Or, in another configuration, the orthodontist might vibrate both of areas A and D. And in yet another configuration, the orthodontist might vibrate all areas from A to H, perhaps at different frequencies or amplitudes or at different times.

The new invention provides an advantage of being more efficient (only the area needed for movement is vibrated) and also allows the possibility of enhanced efficacy since only the area needed is vibrated (vibration of the whole bite-plate may provide some negative feedback to the system since the whole area is vibrated, instead of only the area where faster movement is needed).

In order to achieve differential vibration of teeth, a vibrator motor must be adjacent to those teeth. Therefore, the motor should be very small. However, a large number of very small vibrating motors are available, as shown in the table below. Many of the small vibrators currently used in cell phones and pagers are small motors with an offset weight that causes the motor to vibrate as the shaft turns and the weight pulls the motor from one side to the other. However, newer piezoelectric motors are being developed that would be preferred for use in the invention since they are even smaller and there are no moving parts.

| Company | Catalog | Size | Specifications |
|---|---|---|---|
| Surplus Traders | MF820 | 8 × 4 mm (0.315 × 0.1575 inches) | 1.5 to 4.5 VDC weighted shaft |
| Surplus Traders | MF918 | 0.45 × 0.16 inches | 1 VDC to 5 VDC 18 ohms Weighted shaft |
| Motorola | G13566 | 0.44 × 0.18 inches | 1 VDC to 9 VDC 10 ohms Weighted shaft |
| Surplus Traders | MF835 | 0.45 × 0.24 inches | 1.3 Vdc 100 mA Weighted shaft |
| Elliptec AG | NA See U.S. Pat. No. 6,870,304 | 10 × 3 × 2 mm | 3-6 volts piezoelectric motor |

-continued

| Company | Catalog | Size | Specifications |
|---|---|---|---|
| Matsushita | V0296A | 0.24 inch diameter | 1.5 VDC Weighted shaft |
| Surplus Traders | ME235 | 0.24 × 0.5 inches | 1.5 to 3 VDC 62 mA weighted shaft |
| Precision Microdrives | 304-002 | 4 m × 8 mm | 2.3 VDC to 3.6 VDC 100-120 mA 11000 rpm Weighted shaft |

In addition to electromagnetic motors and piezoelectric motors, other motor types can be used including mechanical actuators, ultrasonic motors and the like. Vibrations may be oscillating, random, directional, circular, and the like. Vibrators are well within the skill of the art, and several are described in the patent literature (and commercially available as seen above). For example, US2007299372, US2007255188, US2007208284, US2007179414, US2007161931, US2007161461, US2006287620, each incorporated by reference, describes various massagers (vibrators) and their motors.

Piezoelectric vibrator and piezoelectric motors can be generated using a variety of compositions and electrical properties that convert electrical energy to mechanical motion. In one embodiment piezoelectric crystals or ceramics can be generated in a variety of sizes and shapes that will alter the frequency of vibration and voltage required. Piezoelectric materials include quartz, mica, calcite, apatite, topaz, berlinite (AlPO4), tourmaline, Rochelle salt, barium titanate (BaTiO3), lead titanate (PbTiO3), lead zirconate titanate (Pb[ZrxTi1-x]O3 or PZT), potassium niobate (KNbO3), lithium niobate (LiNbO3), lithium tantalate (LiTaO3), sodium tungstate (NaxWO3), Ba2NaNb5O5, Pb2KNb5O15, and piezoelectric polymers like polyvinylidene fluoride (PVDF). Commercially available piezoelectric vibrators can be obtained from a variety of custom manufacturers' including TRS Technologies, Inc. (State College, Pa.) and Omega Piezo (State College, Pa.), as well as a multitude of electronic suppliers including Electronic Supply Company, Inc. (Kansas City, Mo.), All Electronics Co. (Van Nuys, Calif.), Radio Shack® and the like.

Generally speaking, the vibrators are placed inside a bite plate at the desired location so that it is adjacent to a tooth while in use (e.g. along the occlusal edge or surface of the bite plate or on the lingual or facial edges or phalanges of a bite plate). The device can include vibrators at all positions, or can have removable motors that can be placed at desired positions and locked in place. When weighted shaft motors are employed in the invention, it is preferred that the motor be placed with the weight pointing towards the midline, thus minimizing bulk on the facial side. The battery may be placed externally, but in a preferred embodiment is placed internally at or near the midline of the bite plate, thus surrounded by teeth, and/or can be adjacent to the teeth but on the lingual side thereof. In the preferred embodiment, the battery is a small disc shaped battery, such as those used in watches and are generally known as coin cell batteries.

Likewise, the processor can also be placed internally, at or near the midline, but in those more sophisticated embodiments can be placed externally, as in U.S. application Ser. Nos. 11/773,849, 11/773,858, and 61/040,777. This allows for more capabilities to be included with the processors, such as a data port, user interface, and the like. In a preferred embodiment, the entire device is self-contained within the bite plate, and the device is programmed for each user by wireless communication with the processor.

The bite plate itself is hermetically sealed or housed so that the user cannot contact the motors or circuits and they are likewise protected from moisture. In a preferred embodiment, the device is coated with a soft polymeric coating, such as silicone rubber, leaving only a small access port for the battery, and the device is pressure activated. Other smooth polymeric material can be used to seal the bite plate, such as polyethylene (PE), high density PE (HDPE), polycarbonate, polyurethane, polypropylene (PP), polyvinylchloride (PVC), polymethyl methacrylate, polyvinylidene fluoride, polyesters, acrylics, vinyl, nylon, rubber, latex, Teflon, or similar material. Preferably, the polymer will not have an objectionable taste and will be FDA approved, such as silicone rubber, polypropylene, HDPE, and the like. The housing can also comprise two plastics, and inner layer for strength and structural integrity, and a more pleasing outer coating for patient compliance.

Depending on which teeth or regions of dentition that need to be treated, different bite plate shapes are possible. However, generally, the bite plate is shaped to contact the occlusal surface of all teeth, and thus a lingually shaped bite plate or U shaped bite plates are preferred. Alternatively, the bite plate may cover only a portion of the dentition, thus being restricted to fewer teeth in use.

When removable motors are employed in the invention, the bite plate is replaced with a U-shaped dental guide that contacts the facial side of the teeth. The removable motors slide over the dental guide, and are then locked into place as needed for each patient. In this embodiment, pressure activated motors are preferred, and the processor may be eliminated, thus decreasing the cost and complexity of the device.

Ideally, the bite plate should contact the maximum surface area of the target teeth in order to optimize the transfer of vibrational forces to each tooth. Thus, in preferred embodiments, the bite plate is customized to fit the patient's dental arches. This can be done for each patient, or an array of sizes can be pre-manufactured for selection by the dental practitioner. The bite plate can also have one or more perpendicular edges or phalanges, said edges being positioned to contact the facial and lingual surface of the teeth and possibly even the gum line.

It may also be required to modify the bite plate to accommodate misaligned teeth. This can be done by adding or subtracting material from the bite plate (or housing) as needed. In another embodiment, the coating material of the bite plate is heat sensitive, allowing customization in much the same way that "boil and bite" commercial tooth guards are customized by each user. In this embodiment, patient comfort is maximized, and yet the bite plate contacts even the most irregular of bite surfaces.

Additionally, it will be possible to use coatings of different hardness to isolate the vibration from, for example, the upper teeth, by using a very soft, malleable coating on the top surface of the bite plate, thus deadening the vibration in this direction. The lower surface may be a harder plastic that transmits vibration more effectively.

The processor controls the vibratory source, and can be programmed to change the force, its direction, frequency, wave form, amplitude, duration or any other operating parameter. In a preferred embodiment the processor actively communicates with the user to provide input related to device use, duration of use, and/or biting force, too hard or not hard enough.

The device can be programmable and have memory capacity, as described in co-pending U.S. application Ser. Nos. 11/773,849 and 11/773,858, incorporated herein by reference. Thus, the frequency, amplitude and duration can be modified as needed, and the usage of the device monitored by the dentist or patient. Communication with other processors can be direct or wireless.

In one embodiment, the interior of the bite plate contains a switch that is activated when sufficient pressure is applied to the bite plate. Thus, no additional on/off switch is needed and the vibrator automatically commences when the bite plate is in use.

In another embodiment, the processor can send and/or receive information from a remote processor. The processor communicates with a remote computer via internet, phone, wireless, infrared, satellite, cellular, cable, modem, or other form of electronic communication. The processor can run software that captures usage frequency and duration. In yet another aspect, a method for recording the compliant use of an orthodontic device, where the device has electronic media that captures information about usage, tooth position, and/or device function for download and analysis.

Batteries, either non-rechargeable or rechargeable, or other electric source can drive the vibrational source. If a rechargeable battery is used it can be charged from any type of power source including USB ports, RS-232 ports, FireWire ports, transformer, or unique docking power source, for example.

The device can be used alone, or in combination with other orthodontic devices. Thus, the user of traditional orthodontic fixed appliances or aligner based treatments can use the device to speed remodeling, or a new patient can employ the device alone provided that the user's application of the device is of sufficient regularity so as to achieve its intended effect.

The device of the invention can be used in a variety of oral and maxillofacial applications including malocclusion, trauma repair, temporomandibular joint and muscle disorders (TMJDs), Lefort fractures, craniofacial anomalies, bone defects, dentofacial deformities, dental implants, as well as tooth, muscle, nerve, tendon, ligament, bone, and connective tissue repair.

Thus, the invention also includes a method for movement of an individual tooth or groups of teeth by applying differential vibration to selected areas of a bite plate at frequencies between 0.1 to 1,000 Hz (or 5-150 or 10-50 Hz) and a force of 0.01-3.0 Newtons (or 0.1-1 or 0.2-0.6 Newtons) for a period of 1-60 minutes, preferably about 1-30 or 1-10 minutes. This is followed by a period of recovery, ranging from 2-24 hours, preferably from 4-12 hours, and the cycle is repeated until one or more teeth are successfully moved. More particularly, the orthodontic appliance of the invention has a vibrational source capable of providing a vibratory force at a frequency of between 0.1 to 1,000 Hz and a force of 0.01-3.0 Newtons. Patients are not expected to tolerate forces greater than 3N, and may have difficulty tolerating forces between 1N and 3N.

connecting to battery (B). A housing (8) surrounds the device, and has a dental guide slot (4) through which the dental guide is passed (not shown). Fastener 6 locks the device to a particular location along the dental guide.

Figure 3:
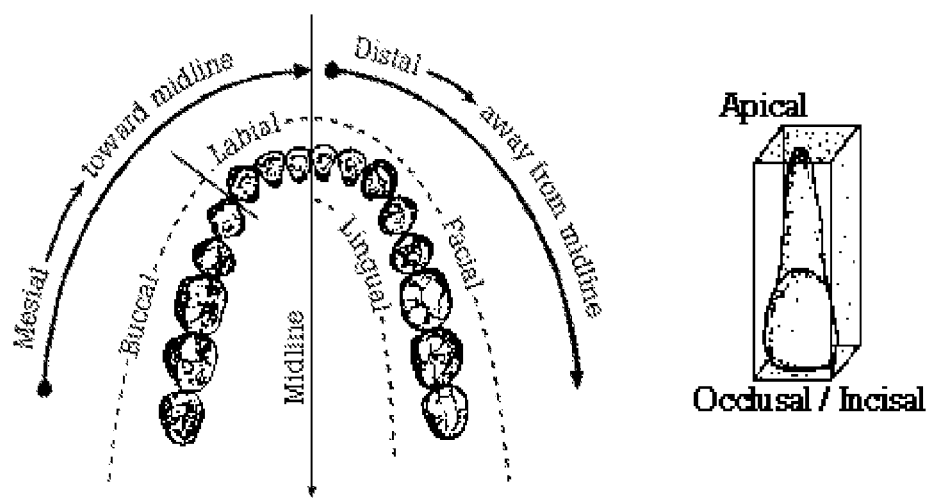
Figure 3:
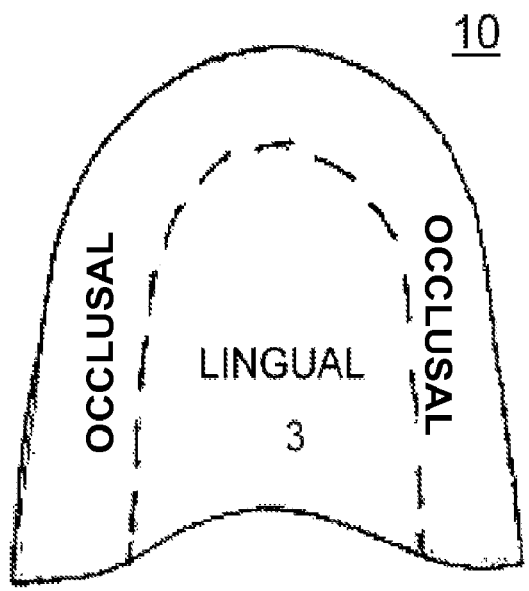

FIG. 3 is a diagram showing dental anatomy, and a top view of a differential vibrator 10 with bite plate 3 showing the occlusal edge and lingual center.

DESCRIPTION OF EMBODIMENTS OF THE INVENTION

Referring now to the drawings in greater detail, there is illustrated therein various vibratory dental appliances.

EXAMPLE 1

Differential Vibrational Dental Plate

Figure 1:
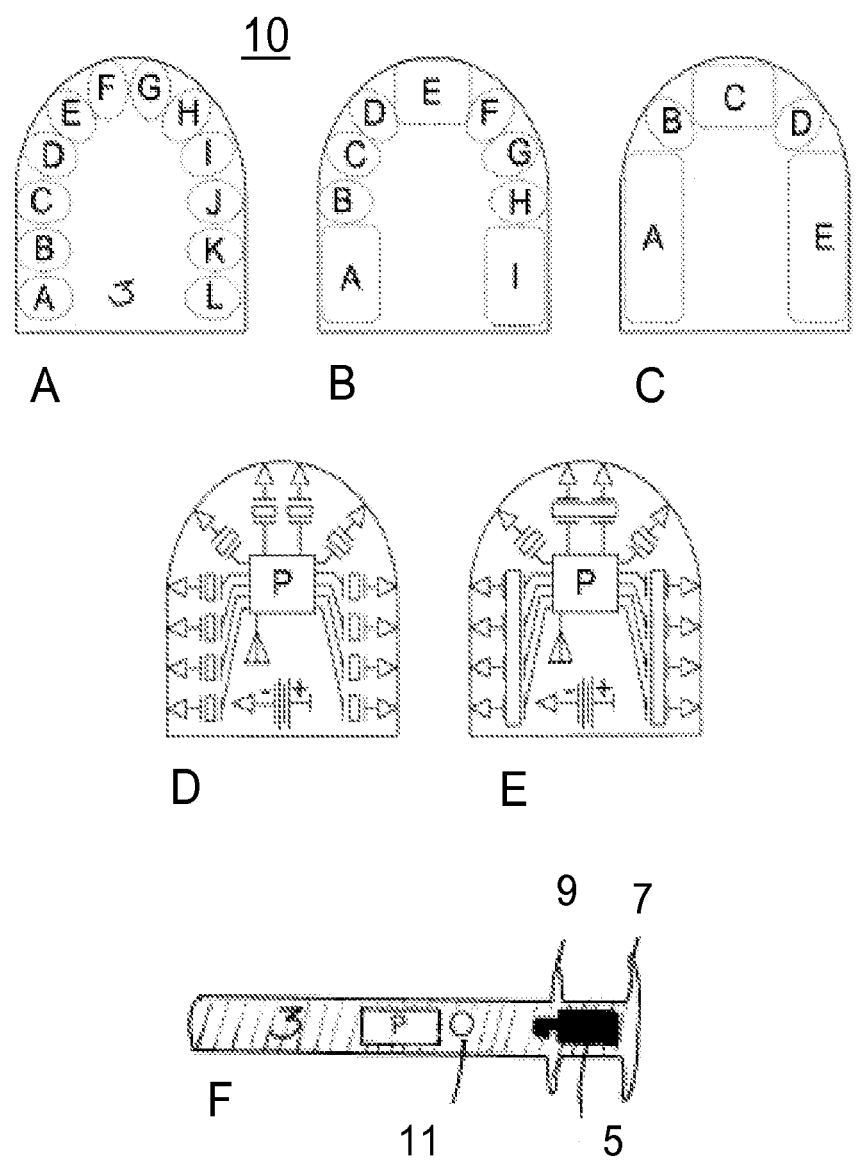
FIGS. 1A, B, C shows three embodiments of an orthodontic treatment device with different zones (A-L, A-I or A-E) that can be vibrated.
FIG. 1D shows the circuit diagram for FIG. 1A
FIG. 1E is the circuit diagram for FIG. 1C., where the power source and processor (P) are placed lingually in each embodiment.
FIG. 1F shows a bite plate 3 in cross section (across the midline) with vibrating motor 5 and illustrating facial edge 7 and lingual edge 9 designed to contact the front and back of teeth. Also shown are the processor P and battery 11 (circuits omitted).

FIG. 1 shows one embodiment of a differential vibration dental plate 10. The device 10 has an intraoral bite plate 3 that lingually shaped for insertion into a patient's mouth. Inside the bite plate 3 are tiny vibration motors (A-L) situated to contact the various tooth zones. Alternatively, a continuous piezoelectric motor can differentially apply vibrational force to the various zones.

The device 10 is clamped down by the patient's jaw on the bite plate 3 to secure it between the dental arches. The vibration sources A-L in this embodiment are activated by pushing a button (not shown) on the bite plate, or alternatively can be activated by patient bite pressure thus closing the relevant circuit.

The bite plate is covered with a polymeric molded coating (not shown) or housing (not shown) in order to hermetically seal the motors. An access valve (not shown) can provide access for replacement of the batter (P).

Using a continuous piezoelectric circuit, a small section of a piezoelectric circuit may be excited or a variety of different areas may be excited. In Example 1D-E, the two circuits could give similar or different vibration patterns. FIG. 1D shows a battery, processor, and circuits A-L corresponding to the pads in FIG. 1A. The processor may be a simple switch or a complex series of components. The processor may optionally one or more components selected from a memory device, program for adjusting vibration, a motor, one or more sensors, one or more batteries, one or more piezoelectric devices, a USB and/or USB 2 port or cord, and an antenna.

The optional antennae, shown in FIG. 4D-E as an inverted triangle, may be used for one or two way communication, either sending information from the mouthpiece to a receiver, receiving information at the mouthpiece, or receiving instructions and sending compliance data from the mouthpiece.

With wireless telemetry, the central processor can be externally programmed, e.g., by the orthodontist) to differentially activate certain vibration motors, and this programming can be performed once and saved for the patients continued use. The various vibration motors can be also differentially activated with an on/off button under the polymeric coating.

EXAMPLE 2

Customizable Differential Vibrational Dental Plate

Figure 2:
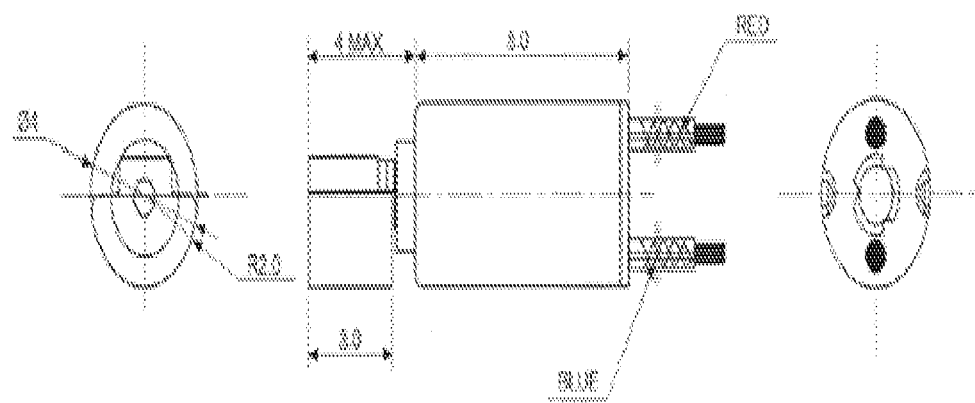
FIG. 2A shows a common vibrating motor.
FIG. 2B shows the same motor (M) with offset weight (W) and leads (2)

The embodiment described in Example 1 has vibration motors at all quadrants of the bite plate, and relies on differential programming or activation to achieve differential vibration. However, this embodiment has two disadvantages, namely, cost increases because each vibration motor and the associated circuitry contribute to cost. Secondly, since the bite plate covers all of the teeth, there is some transmission of vibration from the activated motors to other teeth. This embodiment solves these two difficulties by having a universal dental guide as opposed to dental plate, that is a U-shaped wire or band that fits on the facial surface of the teeth, and to which one or more vibration motors can be placed and affixed at the desired location (see FIG. 2B).

Preferably the dental guide is made of metal or other slightly deformable material, so that the curvature of the dental guide can be adjusted for each patient. However, if metal, the guide is preferably covered with a polymeric coating so the patient does not contact any metal. Single vibration motors (M) are operably connected to a battery (B), such as a coin cell battery, of appropriate voltage, and the entire device is housed inside a polymeric or resin housing (8) that slides over the dental guide (see e.g., slot (4)) and is locked into position (see e.g., fastener (6)) at the exact location of the tooth to be treated. One or more of these individual vibration motors can thus be placed on the dental guide at the appropriate location for treatment. As above, the on/off switch can be an external button or an internal pressure activated switch, depending on the flexibility of the housing.

The locking means can be any suitable device for holding the vibrator in position, including small screws, bolts, clamps, rivets, pins, glue, ridges, clips, brackets, and the like. The locking means can fit directly adjacent or through the housing, or can sit to either side, thus blocking further motion of the vibrator. In another variation, the housing comes in upper and lower halves that lock together over the dental guide, in a snap lock manner, thus eliminating the need for a separate locking means. In this variation, the orthodontist places the lower half of the vibration motor in the correct location, and locks it into place by snapping on the upper half of the housing to the lower half.

The following references described herein are expressly incorporated in their entirety:
U.S. Pat. No. 4,883,046
U.S. Pat. No. 4,244,688
U.S. Pat. No. 4,348,177
U.S. Pat. No. 4,382,780
U.S. Pat. No. 5,030,098
U.S. Pat. No. 5,967,784
U.S. Pat. No. 6,632,088
U.S. Pat. No. 6,684,639
U.S. Pat. No. 6,832,912
U.S. Pat. No. 7,029,276
U.S. Pat. No. 7,163,399
U.S. Pat. No. 7,192,281
JP2007260158
U.S. Ser. No. 11/773,849
U.S. Ser. No. 11/773,858
US61/040,777
US2007299372
US2007255188
US2007208284
US2007179414
US2007161931
US2007161461
US2006287620

What is claimed is:
1. A differential vibration orthodontic device, comprising:
a lingually shaped bite plate having an occlusal arch shaped portion to be positioned between the occlusal surfaces of an upper and lower jaw and a mid portion that extends across the arch between the occlusal surfaces on each side of the arch, a plurality of vibration motors placed on the portion of the bite plate, wherein said vibration motors are capable of providing a vibratory force at a frequency of between 0.1 to 1000 Hz and a force of 0.01-3 Newtons, a battery and a processor for differentially vibrating the plurality of vibrational motors, wherein the processor allows for each of the vibrational motors to be independently vibrated differently from the other vibrational motors and wherein the battery and the processor are positioned in the mid portion of the bite plate, and wherein the bite plate is hermetically sealed and has an access port for accessing said battery.

2. The differential vibration orthodontic device of claim 1, wherein the processor further includes a wireless data communicator.

3. The differential vibration orthodontic device of claim 1, wherein the bite plate is hermetically sealed with silicon rubber.

4. The differential vibration orthodontic device of claim 1, wherein the bite plate is hermetically sealed with polyurethane.

5. The differential vibration orthodontic device of claim 1, wherein the vibration motors are electromagnetic motors having a weighted shaft.

6. The differential vibration orthodontic device of claim 1, wherein the vibration motors are piezoelectric motors.

7. The differential vibration orthodontic device of claim 1, wherein the access port provides access for said battery and said processor.

8. A differential orthodontic vibrator, comprising:

a lingually shaped bite plate having an occlusal arch shaped portion to be positioned between the occlusal surfaces of an upper and lower jaw and a mid portion that extends across the arch between the occlusal surfaces on each side of the arch, a plurality of vibrators on the occlusal portion of the bite plate, a battery and processor for differentially vibrating said plurality of vibrators, wherein the processor allows for each of the vibrational motors to be independently vibrated differently from the other vibrational motors and wherein said battery and processor are positioned in the mid portion of the bite plate and the processor further includes means for wireless communication; and wherein the bite plate is coated to exclude moisture and has an access port for accessing said battery and said processor.

9. An intraoral differential orthodontic vibrator, comprising:

a deformable U-shaped intraoral dental guide;

one or more removable housings located on said intraoral dental guide, said one or more removable housings each containing a vibrator operatively coupled to a battery and an activation switch, wherein said one or more removable housings are intraoral and wherein each of the vibrational motors can be independently vibrated differently from the other vibrational motors; and means for locking said one or more removable housings to a particular location on said intraoral dental guide, wherein said means for locking is intraoral.

10. The differential orthodontic vibrator of claim 9, wherein the intraoral dental guide is metal and covered with a polymeric coating.

11. The differential orthodontic vibrator of claim 9, wherein the vibrator is an offset weight DC motor.

12. The differential orthodontic vibrator of claim 9, wherein the housing comprises an injection molded polymer and said locking means is a screw.

13. The differential orthodontic vibrator of claim 12, wherein the injection molded polymer comprises silicone rubber.

* * * * *